(12) United States Patent
Melvin

(10) Patent No.: US 6,409,760 B1
(45) Date of Patent: Jun. 25, 2002

(54) DEVICE AND METHOD FOR RESTRUCTURING HEART CHAMBER GEOMETRY

(75) Inventor: David B. Melvin, Loveland, OH (US)

(73) Assignee: University of Cincinnati, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/598,424

(22) Filed: Jun. 21, 2000

Related U.S. Application Data

(63) Continuation of application No. 09/035,710, filed on Mar. 5, 1998.

(51) Int. Cl.[7] .................................................. A61F 2/24
(52) U.S. Cl. .......................................... 623/3.1; 600/37
(58) Field of Search ................................. 623/3.1, 2.42; 600/37, 153, 16–18; 606/153

(56) References Cited

U.S. PATENT DOCUMENTS

| 2,826,193 A | 3/1958 | Vineberg |
| 3,053,249 A | 9/1962 | Smith |
| 3,455,298 A | 7/1969 | Anstadt |
| 3,513,836 A | 5/1970 | Sausse |
| 3,590,815 A | 7/1971 | Schiff |

(List continued on next page.)

FOREIGN PATENT DOCUMENTS

| EP | 0119357 | 9/1984 | |
| EP | 0 583 012 | 2/1988 | |
| EP | WO 98/29041 | * 7/1998 | ............. A61F/1/00 |
| SU | 1191076 | 11/1985 | |
| WO | WO 99/30647 | 6/1999 | |
| WO | WO 99/53977 | 10/1999 | |
| WO | WO 00/02500 | 1/2000 | |
| WO | WO 00/06026 | 2/2000 | |
| WO | WO 00/06027 | 2/2000 | |
| WO | WO 00/06028 | 2/2000 | |
| WO | WO 00/16700 | 3/2000 | |

OTHER PUBLICATIONS

International Search Report for Intern'l Application No.: PCT/US 99/22769 dated Mar. 16, 2000.
International Search Report for Intern'l Publication No.: WO9724116.
U.S. patent application No. 08/992,316; filed Dec. 17, 1997.
U.S. patent application No. 09/064,370; filed Apr. 22, 1998.
U.S. patent application No. 09/114,510; filed Jul. 13, 1998.
U.S. patent application No. 09/114,757; filed Jul. 13, 1998.
U.S. patent application No. 09/123,977; filed Jul. 29, 1998.
U.S. patent application No. 09/157,486; filed Sep. 21, 1998.
Tellides et al., *Journal of Heart and Lung Transplantation*, (1981) 17:1, Abstract No. 180, p. 89.

(List continued on next page.)

*Primary Examiner*—David H. Willse
*Assistant Examiner*—Suzette J. Jackson
(74) *Attorney, Agent, or Firm*—Ratner & Prestia

(57) ABSTRACT

A static device for use with the heart that has a plurality of members configured to be positioned adjacent the epicardial surface of the heart. The members are joined by at least one connector wherein the members are fixed in a spatial or spaced relationship relative to each other such that a portion of the heart wall is displaced inwardly.

The member(s) can be configured in a rectangular shape, and preferably includes an inner surface having a curved configuration. In one embodiment, the device can have first and second member that are positioned in a spaced relationship relative to each other about 180 degrees apart. The first member is configured to be positioned adjacent the anterolateral surface of the chamber, and the second member configured to be positioned adjacent the posteromedial surface of the chamber.

50 Claims, 6 Drawing Sheets

U.S. PATENT DOCUMENTS

| | | | |
|---|---|---|---|
| 3,613,672 A | | 10/1971 | Schiff |
| 3,668,708 A | | 6/1972 | Tindal |
| 3,713,439 A | | 1/1973 | Cabezudo |
| 3,791,388 A | | 2/1974 | Hunter et al. |
| 3,827,426 A | | 8/1974 | Page et al. |
| 3,983,863 A | | 10/1976 | Janke et al. |
| 4,192,293 A | | 3/1980 | Asrican |
| 4,536,893 A | * | 8/1985 | Parravicini ............... 623/3.1 |
| 4,621,617 A | | 11/1986 | Sharma |
| 4,690,134 A | | 9/1987 | Snyders |
| 4,809,676 A | | 3/1989 | Freeman |
| 4,846,831 A | | 7/1989 | Skillin |
| 4,904,255 A | | 2/1990 | Chareier et al. |
| 4,936,857 A | | 6/1990 | Kulik |
| 4,957,477 A | | 9/1990 | Lundback |
| 5,109,843 A | | 5/1992 | Melvin et al. |
| 5,119,804 A | | 6/1992 | Anstadt |
| 5,131,905 A | | 7/1992 | Grooters |
| 5,139,517 A | | 8/1992 | Corral |
| 5,169,381 A | | 12/1992 | Snyders |
| 5,192,314 A | | 3/1993 | Daskalakis |
| 5,201,880 A | | 4/1993 | Wright et al. |
| 5,256,132 A | | 10/1993 | Snyders |
| 5,258,021 A | * | 11/1993 | Duran ...................... 623/3.1 |
| 5,334,217 A | | 8/1994 | Das |
| 5,345,949 A | | 9/1994 | Shlain |
| 5,358,519 A | | 10/1994 | Grandjean |
| 5,370,685 A | | 12/1994 | Stevens |
| 5,383,840 A | | 1/1995 | Heilman et al. |
| 5,385,528 A | | 1/1995 | Wilk |
| 5,484,391 A | | 1/1996 | Buckman, Jr. et al. |
| 5,487,760 A | | 1/1996 | Villafana |
| 5,533,958 A | | 7/1996 | Wilk |
| 5,571,176 A | | 11/1996 | Taheri |
| 5,593,424 A | * | 1/1997 | Northrup, III ............. 606/232 |
| 5,655,548 A | * | 8/1997 | Nelson et al. ............. 128/898 |
| 5,702,343 A | | 12/1997 | Alferness |
| 5,709,695 A | | 1/1998 | Northrup, III |
| 5,713,954 A | | 2/1998 | Rosenberg et al. |
| 5,738,626 A | | 4/1998 | Jarvik |
| 5,738,627 A | | 4/1998 | Kovacs et al. |
| 5,749,883 A | | 5/1998 | Halpern |
| 5,800,528 A | * | 9/1998 | Lederman et al. ........... 623/3.1 |
| 5,824,071 A | | 10/1998 | Nelson et al. |
| 5,957,977 A | * | 9/1999 | Melvin ........................ 623/3 |
| 5,961,440 A | * | 10/1999 | Schweich, Jr. et al. ....... 600/16 |
| 6,019,722 A | | 2/2000 | Spence et al. |
| 6,045,497 A | | 4/2000 | Schweich, Jr. et al. |
| 6,050,936 A | * | 4/2000 | Schweich, Jr. et al. ....... 600/37 |
| 6,059,715 A | | 5/2000 | Schweich, Jr. et al. |
| 6,077,214 A | | 6/2000 | Mortier et al. |
| 6,190,408 B1 | * | 2/2001 | Melvin ...................... 623/3.1 |
| 6,214,047 B1 | * | 4/2001 | Melvin ........................ 623/3 |
| 6,221,103 B1 | * | 4/2001 | Melvin ...................... 623/3.1 |

OTHER PUBLICATIONS

Kawaguchi et al., *Journal of heart and Lung Transplantation*, (1998) 17:1, Abstract No. 181, p. 89.

Dowling et al., *Journal of Heart and Lung Transplantation*, (1998) 17:1, Abstract No. 76, p. 62.

Khoynezhad et al., *Journal of Heart and Lung Transplantation*, (1998) 17:1, Abstract No. 77, p. 62.

Batista et al., *Ann. Thorac. Surg.*, (1997) 64, pp. 634–638.

Melvin, D., "Ventricular Radius–Reduction Without Resection: A Computational Assessment," *ASAIO Journal* (Abstract), vol. 44, No. 2, p. 57A, Mar. 5, 1998.

Melvin, D., "Ventricular Radius–Reduction Without Resection: A Computational Assessment," *ASAIO Annual Meeting* (Poster), Jun. 1998.

Melvin, D.B.; Melvin, A.J.; Trossman, C.A.; and Glos, D.L., "Reduction of Ventricular Wall Tensile Stress by Geometric Remodeling Device," *ASAIO Journal* (Abstract), vol. 45, No. 2, p. 166, Mar. 17, 1999.

Melvin, D.B.; Melvin, A.J.; Trossman, C.A.; and Glos, D.L., "Reduction of Ventricular Wall Tensile Stress by Geometric Remodeling Device," *ASAIO Annual Meeting* (Poster), Jun., 1999.

Boyer, M., "SDRC Agreement Could Hasten Medical Advances," *The Cincinnati Enquirer*, Mar. 2, 1999.

Miller, N., "SDRC gives its software to BIO/START," *The Cincinnati Post*, Mar. 2, 1999.

Bonfield, T., "CardioClasp may help biomedicals," *The Cincinnati Enquirer*, Nov. 7, 1999.

Bonfield, T., "Surgeon's invention could help thousands—Tests begin on device to treat heart disease," *The Cincinnati Enquirer*, Nov. 7, 1999.

Vaccariello, L., "Who Will Invent the Cures?" *Cincinnati*, Dec. 1999, p. 64.

"SDRC Agreement to Speed Medical Advances," *University of Cincinnati News & Info*, Apr. 1999 Newsletter.

\* cited by examiner

DEVICE AND METHOD FOR RESTRUCTURING HEART CHAMBER GEOMETRY

This application is a continuation of U.S. patent application Ser. No. 09/035,710, filed Mar. 5, 1998 (status: pending).

TECHNICAL FIELD OF THE INVENTION

The present invention relates to a device and method for treating cardiomyopathies and/or enlarged hearts and more specifically, a device and method for decreasing a heart chamber's wall tension.

BACKGROUND OF THE INVENTION

The natural heart, and specifically, the cardiac muscle tissue of the natural heart (e.g., myocardium) can fail for various reasons to a point where the natural heart cannot provide sufficient circulation of blood for a body so that life can be maintained. More specifically, the heart and its chambers can become enlarged for a variety of causes and/or reasons, including viral disease, idiopathic disease, valvular disease (mitral, aortic and/or both), ischemic disease, Chagas' disease and so forth. As the heart and its chambers enlarge, tension of the walls of the heart's chambers increase and thus, the heart must develop more wall tensile stress to generate the needed pressure for pumping blood through the circulatory system. As a solution for the enlarged natural heart, attempts have been made in the past to provide a treatment to maintain circulation.

One such approach has been to replace the existing natural heart in a patient with an artificial heart or a ventricular assist device. In artificial hearts and/or assist devices, a particular problem stems from the fact that the materials used for the interior lining of the chambers of an artificial heart are in direct contact with the circulating blood, which can enhance undesirable clotting of the blood, build up of calcium, or otherwise inhibit the blood's normal function. Hence, thromboembolism and hemolysis could occur with greater ease. Additionally, the lining of an artificial heart or a ventricular assist device can crack, which inhibits performance, even if the crack is at a microscopic level. Moreover, these devices must be powered by a source which can be cumbersome and/or external to the body. Drawbacks have limited use of these devices to applications having too brief a time period to provide a real lasting benefit.

An alternative procedure is to transplant a heard from another human or animal into a patient. The transplant procedure requires removing an existing organ (i.e., the natural heart) for substitution with another organ (i.e., another natural heart) from another human, or potentially, from an animal. Before replacing an existing organ with another, the substitute organ must be "matched" to the recipient, which can be, at best, difficult and time consuming to accomplish. Furthermore, even if the transplanted organ matches the recipient, a risk exists that the recipient's body will reject the transplanted organ and attack it as a foreign object. Moreover, the number of potential donor hearts is far less than the number of patients in need of a transplant. Although use of animal hearts would lessen the problem with fewer donors than recipients, there is an enhanced concern with rejection of the animal heart.

In an effort to use the existing natural heart of a patient, other attempts have been made to reduce wall tension of the heart by removing a portion of the heart wall, such as a portion of the left ventricle in a partial left ventriculectomy procedure (the Batista procedure). A wedge-shaped portion of the ventricular muscle has been removed, which extends from the apex to the base of the heart. By reducing the chamber's volume, and thus its radius, the tension of the chamber's wall is reduced as well. There are, however, several drawbacks with such a procedure. First, a valve (i.e., the mitral valve) may need to be repaired or replaced depending on the amount of cardiac muscle tissue to be removed. Second, the procedure is invasive and traumatic to the patient. As such, blood loss and bleeding can be substantial during and after the procedure. Moreover, as can be appreciated by those skilled in the industry, the procedure is not reversible.

Another device developed for use with an existing heart for sustaining the circulatory function of a living being and the pumping action of the natural heart is an external bypass system, such as a cardiopulmonary (heart-lung) machine. Typically, bypass systems of this type are complex and large, and, as such, are limited to short term use in an operating room during surgery, or to maintaining the circulation of a patient while awaiting receipt of a transplant heart. The size and complexity effectively prohibit use of bypass systems as a long term solution, as they are rarely even portable devices. Furthermore, long term use of these systems can damage the blood cells and blood borne products, resulting in post surgical complications such as bleeding, thromboembolism function, and increased risk of infection.

Medicines, such as vasodilators, have been used to assist in treating cardiomyopathies. For example, digoxin can increase the contractibility of the heart, and thereby enhances emptying of the chambers during systolic pumping. On the other hand, some medicines, such as beta blocking drugs, which decrease the size of the chamber of the heart, also decrease the contractibility of the heart. Other types of medicines, such as angiotensin-converting enzyme inhibitors (e.g., enalopril) can help reduce the tendency of the heart to dilate under the increased diastolic pressure experienced when the contractibility of the heart muscle decreases. Many of these medicines have side effects, such as excessive lowering of blood pressure, which make them undesirable for long term therapy.

As can be seen, currently available treatments, procedures, medicines, and devices for treating end-stage cardiomyopathies have a number of shortcomings that contribute to the complexity of the procedure or device. The current procedures and therapies can be extremely invasive, only provide a benefit for a brief period of time, or have undesirable side effects which can hamper the heart's effectiveness. There exists a need in the industry for a device and procedure that can use the existing heart to provide a practical, long-term use device and procedure to reduce wall tension of the heart, and thus improve its pumping efficiency.

SUMMARY OF THE PRESENT INVENTION

It is the object of the present invention to provide a device and method for treating cardiomyopathies that addresses and overcomes the above-mentioned problems and shortcomings in the thoracic medicine art.

It is another object of the present invention to provide a device and method for treating cardiomyopathies that minimizes damage to the coronary circulatory and the endocardium.

It is still a further another object of the present invention to provide a device and method for treating cardiomyopathies that maintains the stroke volume of the heart.

Another object of the present invention is to provide a device and method for treating cardiomyopathies that supports and maintains the competence of the heart valves so that the heart valves can function as intended.

Still another object of the present invention is to provide a device and method that increases the pumping effectiveness of the heart.

Yet another object of the present invention is to provide a device and method for treating cardiomyopathies on a long term basis.

It is yet still an object of the present invention to provide a device and method for treating cardiomyopathies that does not require removal of any portion of an existing natural heart.

Still a further object of the present invention is to provide a device and method for treating dilated cardiomyopathies that directly reduce the effective radius of a chamber of a heart in systole as well as in diastole.

Additional objects, advantages, and other features of the present invention will be set forth and will become apparent to those skilled in the art upon examination of the following, or may be learned with practice of the invention.

To achieve the foregoing and other objects, and in accordance with the purpose herein, the present invention comprises a static device for use with the heart that has a plurality of members configured to be positioned adjacent the epicardial surface of the heart. The members are joined by at least one connector wherein the members are fixed in a spatial or spaced relationship relative to each other such that a portion of the heart wall is displaced inwardly.

The member(s) can be configured in a rectangular shape, and preferably includes an inner surface having a curved configuration. In one embodiment, the device can have first and second member that are positioned in a spaced relationship relative to each other about 180 degrees apart. The first member is configured to be positioned adjacent the anterolateral surface of the chamber, and the second member configured to be positioned adjacent the posteromedial surface of the chamber.

In an alternative embodiment of the device having first, second and third members, the first, second, and third members are positioned in a spaced relationship relative to each other about 120 degrees apart. The first member is configured to be positioned adjacent the anteroseptal portion of the chamber, the second member is configured to be positioned adjacent the posteroseptal portion of the chamber, and a third member is configured to be positioned adjacent the posterolateral portion of the chamber.

The device also may include a pad adjacent the inner surface, and preferably interposed between the member and endocardial surface. The pad can be made of low durometer solid polymer or plastic or, alternatively, the pad could be a gel-filled or fluid-filled cushion.

The connector of the present invention can also include a chord, such as a heavy braided polymer impregnated polyester suture core with a polyester sleeve, or a heavy monofilament polypropylene or an expanded polytetrafluoroethylene (PTFE, such as the brand Gortex® by W.L. Gore & Co.) suture, which can traverse the heart tissue and/or cavity. The connector of the present invention can also include a generally rigid pin or rod that is configured to be insertable through, and connect with, the members.

In a preferred embodiment, the device of the present invention can include at least one fixation device on the member configured for insertion into the heart. The fixation device can take the form of a pin for penetrating the wall of the heart, or alternatively, a button for positioning adjacent the endocardial surface of the heart and a cord joining the member and the button.

In another alternative embodiment, the device of the present invention can include a generally horseshoe-shaped harness having a first rigid portion configured to be positioned adjacent the anterolateral portion of the chamber, a second rigid portion configured to be positioned adjacent the posteromedial portion of the chamber, and a flexible portion (in a tangent plane) interposed between the first and second portion and configured to be positioned around the apical portion of the heart. A basal connector is configured to be interposed between the first and second rigid portions of the harness, and preferably is configured to be attachable to the annulus of an atrioventricular valve.

In use, the present invention can reduce the wall tension on one of the chambers of the heart. A static brace is affixed to the heart so as to provide the chamber of the heart as at least two contiguous communicating regions, such as sections of truncated ellipsoids, which have a lesser minimum radii than the chamber before restructuring. As such, the brace displaces at least two portions of the chamber wall inwardly from the unrestricted position.

BRIEF DESCRIPTION OF THE DRAWINGS

While the specification concludes with claims particularly pointing out and distinctly claiming the present invention, it is believed the same will be better understood from the following description taken in conjunction with the accompanied drawings in which:

DETAILED DESCRIPTION OF THE PREFERRED EMBODIMENT

Figure 1:
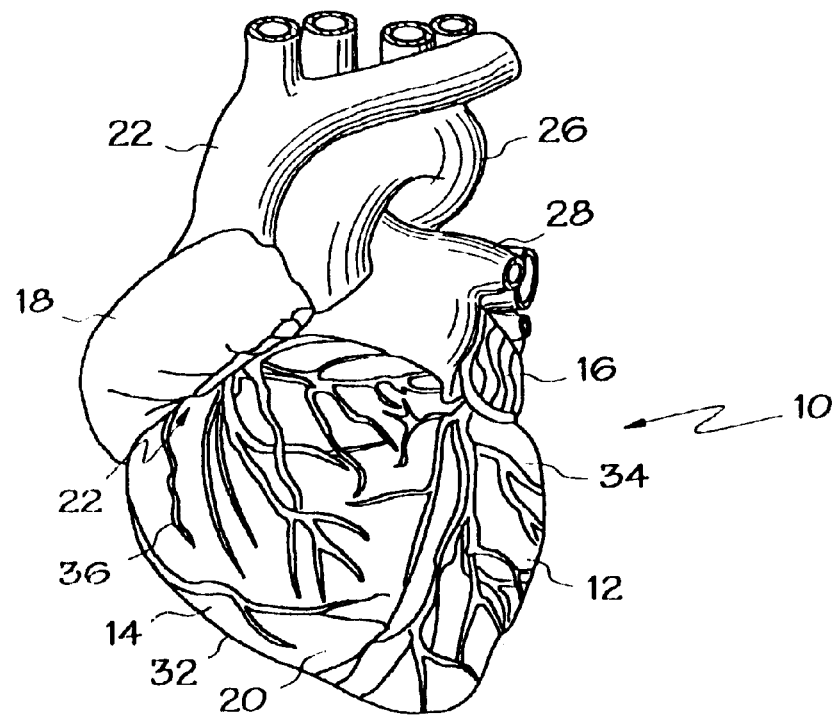
FIG. 1 partial frontal anterior view of an exemplar natural heart.
Figure 2:
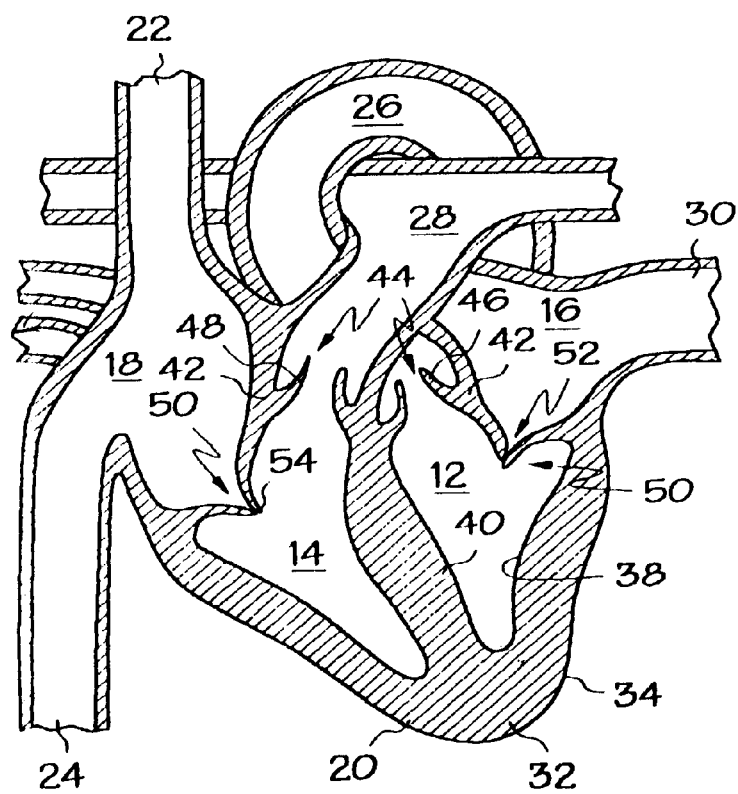
FIG. 2 is a vertical cross sectional view of an exemplar natural heart and blood vessels leading to and from the natural heart.

Referring now to the figures in detail wherein like numerals indicate the same elements throughout the views, an exemplary natural heart, generally indicated in FIGS. 1 and 2 as 10, has a lower portion comprising two chambers, namely a left ventricle 12 and a right ventricle 14, which function primarily to supply the main force that propels blood through the circulatory system, namely the pulmonary circulatory system, which propels blood to and from the lungs, and the peripheral circulatory system, which propels blood through the remainder of the body. A natural heart 10 also includes an upper portion having two chambers, a left atrium 16 and a right atrium 18, which primarily serve as an entryway to the left and right ventricles 12 and 14, respectively, and assist in moving blood into the left and right ventricles 12 or 14. The interventricular wall 40 of cardiac tissue 32 separates the left and right ventricles 12 and 14, and the atrioventricular wall 4 2 of cardiac tissue 32 separates the lower ventricular region from the upper atrium region.

Generally, the left and right ventricles 12 and 14, respectively, each has a cavity 13 and 15, respectively, that is in fluid communication with cavities 17 and 19, respectively, of the atria (e.g., 16 and 18) through an atrioventricular valve 50 (which are each illustrated as closed in FIG. 2). More specifically, the left ventricle cavity 13 is in fluid communication with the left atrium cavity 17 through the mitral valve 52, while the right ventricle cavity 15 is in fluid communication with the right atrium cavity 19 through the tricuspid valve 54.

Generally, the cavities of the ventricles (e.g., 13 and 15) are each in fluid communication with the circulatory system (i.e., the pulmonary and peripheral circulatory systems) through a semilunar valve 44 (which are each illustrated as opened in FIG. 2). More specifically, the left ventricle cavity 13 is in fluid communication with the aorta 26 of the peripheral circulatory system through the aortic valve 46, while the right ventricle cavity 15 is in fluid communication with the pulmonary artery 28 of the pulmonary circulatory system through the pulmonic valve 48.

Blood is returned to the heart 10 through the atria (e.g., 16 and 18). More specifically, the superior vena cava 22 and inferior vena cava 24 are in fluid communication and deliver blood, as it returns from the peripheral circulatory system, to the right atrium 18 and its cavity 19. The pulmonary vein 30 is in fluid communication and delivers blood, as it returns from the pulmonary circulatory system, to the left atrium 16, and its cavity 17.

The heart 10 is enclosed in the thoracic cavity within a double walled sac commonly referred to as the pericardium. Its inner layer is the visceral pericardium or epicardium, and its outer layer is the parietal pericardium. The structure heart 10 is generally made up of, among other materials, cardiac muscle or tissue 32, which has an exterior surface commonly known as the epicardial surface 34 and an interior surface, or endocardial surface 38, that generally defines the cavities (e.g., ventricular cavities 13 and 15, respectively, and atrial cavities 17 and 19, respectively). Coronary arteries 36 on the epicardial surface 34 of the heart 10 provide blood and nourishment (e.g., oxygen) to the heart 10 and its cardiac tissue 32.

By way of a non-limiting example, the present invention will be discussed in terms of embodiments that are used to primarily assist in the restructuring or reconfiguring, and/or operation of the left ventricle (e.g., 12) of the natural heart 10, however, it is noted that the present invention can also be used to assist in the restructuring or reconfiguring, and/or operation of other portions of the natural heart 10, such as either atria (16 and/or 18), or the right ventricle (e.g., 14) of the natural heart 10.

Figure 3:
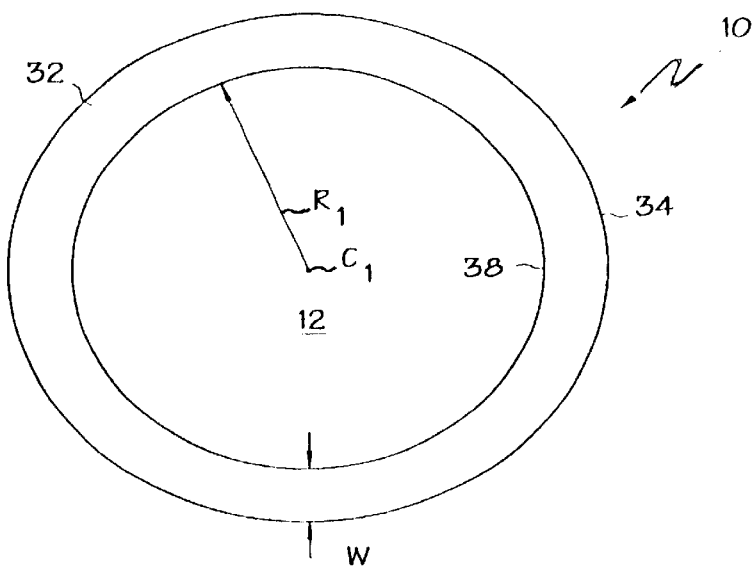
FIG. 3 is a horizontal cross sectional view of an unrestrained left ventricle of the natural heart.

Turning now to FIG. 3, the chambers of the heart 10, including the left ventricle 12, is generally shaped as a hollow truncated ellipsoid having, at any circular cross-section perpendicular to its long axis, a center point "$C_1$" and a radius "$R_1$" extending from center point $C_1$ to the endocardial surface 38. The cardiac tissue 32 of the heart 10 has a thickness "w" which is generally the distance between the epicardial surface 34 and the endocardial surface 38.

Figure 5:
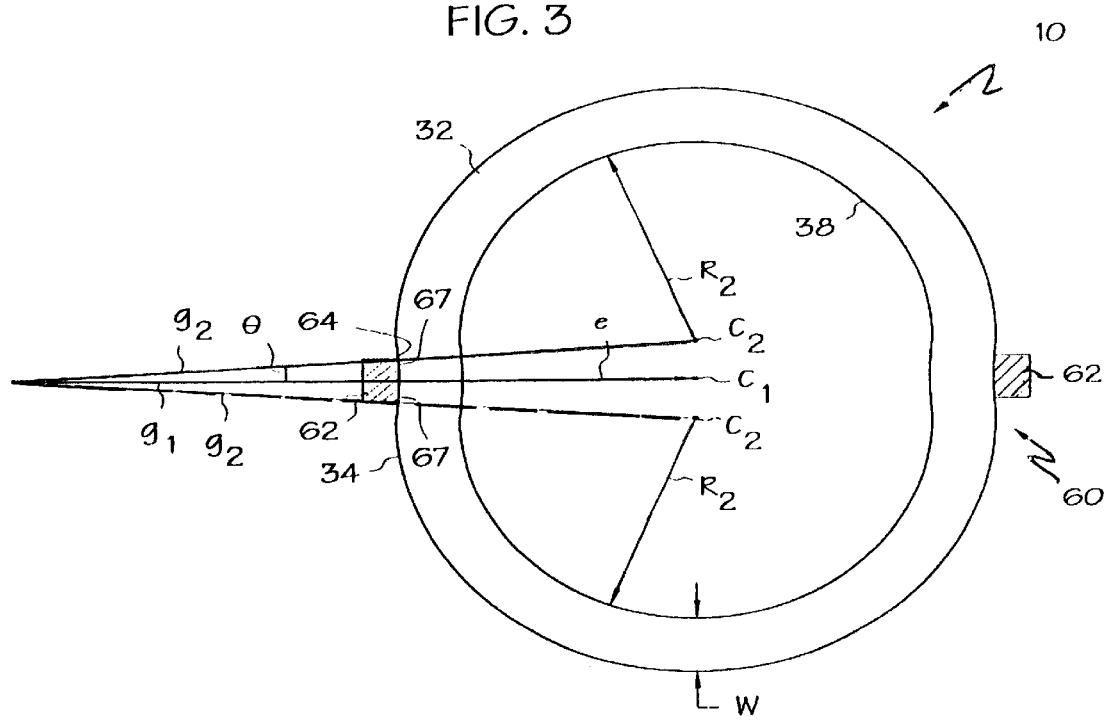
FIG. 5 is a cross sectional view of the device taken along line 5—5 in FIG. 4.
Figure 4:
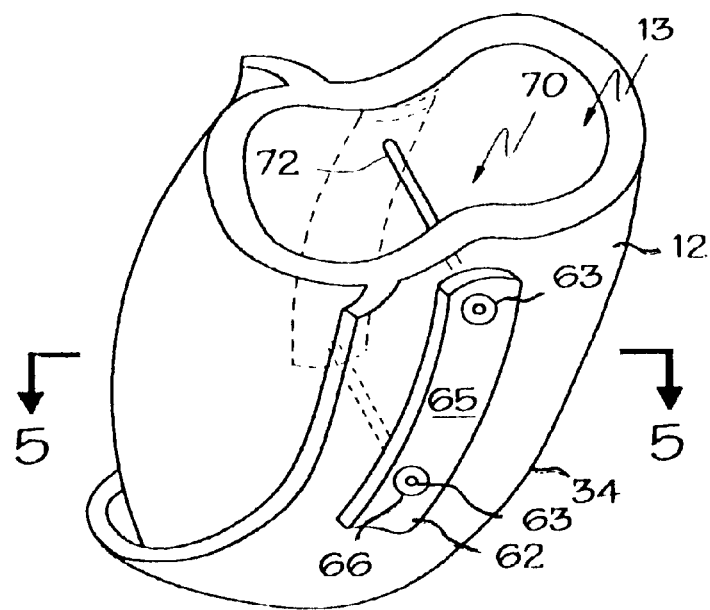
FIG. 4 is a perspective view of a device made in accordance with the present invention and positioned on the left ventricle.

The static device or brace 60 of the present invention exemplified in FIGS. 4 and 5 preferably is configured and positioned relative to the natural heart 10 to displace at least two portions of the cardiac tissue 32 inwardly (see, e.g., FIG. 5) from the unrestricted position, as exemplified in FIG. 3. By displacing portions of the cardiac tissue 32 inwardly, the shape of the chamber (e.g., the left ventricle 12) of the heart 10 is generally restructured or reconfigured from a generally hollow truncated ellipsoid (see, e.g., FIG. 3) to a chamber generally shaped as having at least two continuous communicating portions of truncated ellipsoids (see, e.g., FIG. 5). In generally reconfiguring or restructuring the heart 10 as such, each of the truncated ellipsoids has an adjusted radius "$R_2$," which is preferably shorter than radius "$R_1$."

The device or brace 60 can be static in that it does not actuate or pump the heart 10, but rather, displaces and holds portions of the cardiac tissue 32 in a generally predetermined fixed position as the heart 10 continues to contract (e.g., beat) and pump blood through its chambers and through the body's circulatory system.

The device 60 can include at least two members 62 to assist in restraining or restructuring the left ventricle 12 that are preferably spaced about 180 degrees apart adjacent or on the epicardial surface 34 so as to restructure or reconfigure the left ventricle 12 as having the shape of at least two continuous communicating portions of truncated ellipsoids. One of the members 62 can be configured to be positioned adjacent the anterolateral surface of a chamber (e.g., the left ventricle 12) and the other member 62 can be configured to be positioned adjacent the posteromedial surface of a chamber (e.g., the left ventricle 12).

Each member 62 includes a contact or an inner surface 64 that is preferably curved convex outwardly in a longitudinal plane (see, e.g., FIG. 5) and curved convex inwardly in the transverse plane (see, e.g., FIG. 4) so that member 62 is configured to be positioned adjacent or on the epicardial surface 34 whereby intimate contact can be established and maintained, even during the contraction or beating of the heart 10. Member 62, and its inner surface 64, should be configured so that it is tangent to the portion of the epicardial surface 32 where contact is made and so that the cardiac tissue 32 is altered or displaced in a transverse plane, from its unrestructured inwardly convex shape (see, e.g., FIG. 3) to its restructured concave shape (see, e.g., FIG. 5). The inner surface 64 can be provided as a smooth curved surface having lateral portions 67 such that the epicardial surface 34 may slide along the member 62 during contraction and expansion of the heart 10.

Members 62 are each preferably made of a light weight, generally rigid material that has as a low bending strain under expected levels of stress so that the material has sufficient wear resistance in use while the heart 10 beats, and maintains its desired shape in use adjacent the heart 10. Illustrative examples of materials which may be employed as member 62 include any biocompatible materials such as metals, including titanium or stainless steel or as a suitable polymer, including polyacetal or an ultra high molecular weight polyethylene.

Member 62 can be any desired shape, and can vary according to anatomy and the desired application. Preferably, member 62 has rounded edges and is a generally rectangular shaped object with the length extending in the transverse plane or along the longer axis of the chamber (i.e., extending between the basal portion near the atrioventricular groove 43 (see, e.g., FIG. 1) and apical portion 20 of the heart 10). In a preferred embodiment, member 62 can have a length that varies from about 50% to about 100% of the vertical long axis of the chamber (e.g., 12), approximately from about 4 to about 12 cm, and can vary preferably about 80% of the vertical long axis of the chamber (e.g., 12). Moreover, the member 62 can have a thickness that varies from about 1 mm to about 10 mm, depending on the modules and strength of the material chosen. When metal is used for member 62, the member 62 can preferably have a thickness of about 1 mm, and when a high strength polymer is used for member 62, the member 62 can have a thickness that varies from about 6 mm to about 8 mm.

Member 62 preferably has one or more small apertures 63 extending through its body (e.g., from the inner surface 64 to the outer surface 65) so that a connector 70 can be inserted or threaded therethrough and connected or secured to member 62, as will be explained in detail below. A plurality of apertures 63 can be provided along the length of member 62 to enhance customization of the present invention in a particular use, as desired. Aperture 63 preferably can have a counterbore opening 66 on the outer surface 65 of the member 62 so that, as will be discussed below, the connector 70 can be seated or recessed therein.

Figure 6:
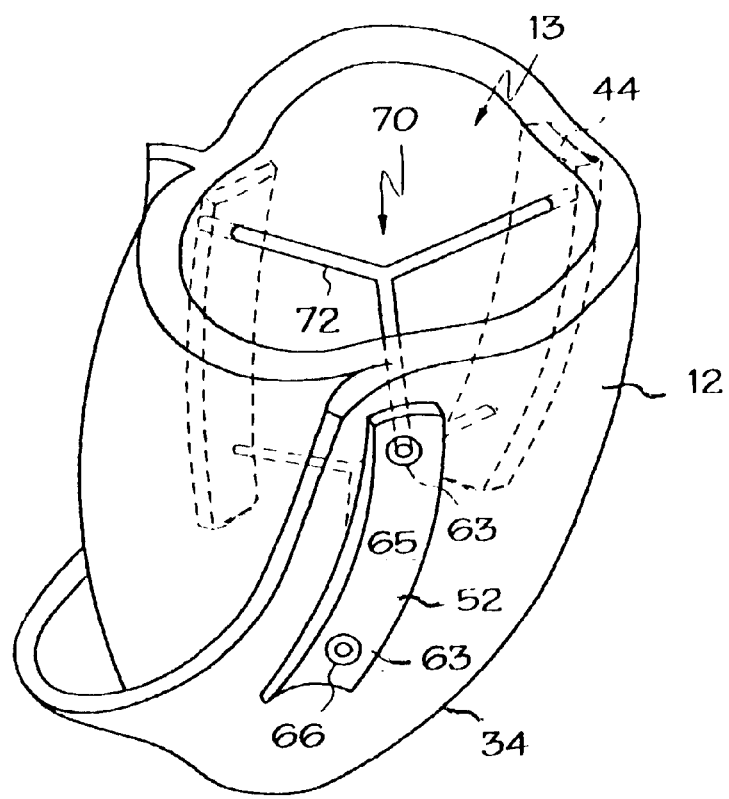
FIG. 6 is a perspective view of an alternative embodiment of a device made in accordance with the present invention and positioned on the left ventricle.

Turning now to FIG. 6, three separate members 62 can also be used in accordance with the present invention to assist in restructuring or reconfiguring the chamber 12 as three continuous communicating truncated portions of ellipsoids, as desired. In such an embodiment, the members 62 are spaced about 120° around the epicardial surface 34. For example, one member 62 is preferably configured to be positioned adjacent the anteroseptal portion of the chamber 12, a second member 62 is preferably configured to be positioned adjacent the posteroseptal portion of the chamber 12, and the third member 62 is preferably configured to be positioned adjacent the posterolateral portion of the chamber 12.

Figure 7A:
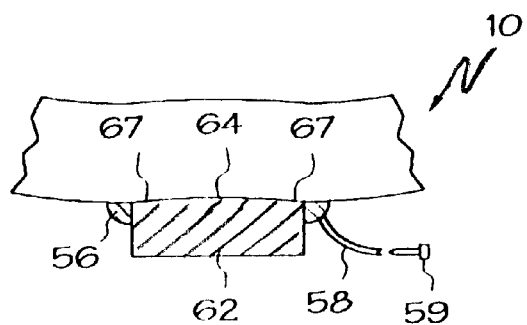
FIG. 7A is a partial horizontal cross sectional view of a pad interposed between the epicardial surface and the member while the heart is at rest.
Figure 7B:
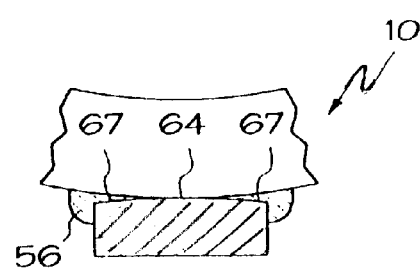
FIG. 7B is a partial horizontal cross sectional view of a pad interposed between the epicardial surface and the member while the heart is contracting.

So that the epicardial surface 34 may separate from member 62 adjacent or at the lateral portions 67 of inner surface 64 without creating substantial negative pressure, a pad 56 can be positioned and/or interposed between the epicardial surface 34 and the inner surface 64. Pad 56 can be, as exemplified in FIGS. 7A and 7B, a fluid-filled or gel-filled pad or cushion, which generally will occupy space laterally beyond the member 62 and the lateral portions 67 of inner surface 64 while the heart 10 is in as a relaxed state. However, as the heart 10 contracts and the wall shortens (see, e.g., FIG. 7B), generally circumferentially (reducing cavity radius), the epicardial surface 34 will "peel away" from the members 62 and the lateral portions 67 of inner surface 64 and thus, fluid or gel in the pads 56 can fill this space so that the inner surface 64 and epicardial surface 34 remain in contact and effect focal restraint whereby the chamber 12 is restructured, as detailed above.

In one embodiment, the pad 56 is a closed system. Alternatively, it is contemplated that pad 56 can be configured such that fluid and/or gel can be added or removed to enhance functionality of the device 60 of the present invention, as desired. For example, one or more lines 58 can be in fluid communication with a chamber in pad 56. Line 58 can extend from pad 56 to an injection port 59, which can be positioned subcutaneous or elsewhere, as desired, for enhanced access. As will be appreciated by those skilled in the art, fluid or gel can be injected into the injection port 59 using a standard syringe and needle, or other device, to increase the size of the pad 56 and/or the pressure within the pad 56, as desired. Alternatively, fluid or gel can be withdrawn as desired.

Alternatively, pad 56 can be as a low durometer polymer such as a plastic or other material (e.g., rubber). In use, as detailed above, the material accommodates and maintains the contact between the member 62, and more specifically its inner surface 64, and epicardial surface 34 and thus, the desired reconfiguration of the heart 10 as the heart 10 beats or deforms.

So that members 62 remains fixed in a spatial or spaced relationship to each other and adjacent or on the epicardial surface 34, as desired, one or more connectors 70 connect or otherwise join the members 62 together. Connector 70 can take the form of various mechanical connectors used in the industry to attach and position prosthetic devices in the body. Exemplar connectors 70 which will be discussed below in some detail, may include a chord (e.g., 72), a pin (e.g., 73, 76) and the like.

Turning back to FIGS. 4 and 6, one or more generally flexible elongated chords 72 can be used to join or attach members 62 together whereby they remain in the desired placement. In one embodiment, chord 72 is sized such that it can be inserted or threaded through an aperture 63, through the cardiac tissue 32, span across the cavity 13, can be inserted into and through the cardiac tissue 32 on the other side of the chamber 12, and joined to the corresponding member 62, preferably through aperture 63. Chord 72 can be joined or affixed to member 62 using devices and techniques known in the industry, such as by providing surgical suture knots and the like adjacent or at the ends of the chord 72, as desired, which can then be recessed in counterbore opening 66.

Chord 72 is generally made of a biocompatible material that preferably inhibits the formation of blood clots and/or enhances tissue integration around the chord 72. Illustrative examples of materials which may be employed as chord 72 may include expanded PTFE, polyester, or polypropylene. Preferably, chord 72 may include PTFE, a braided polymer, such as polyester or a monofilament polypropylene.

Figure 8:
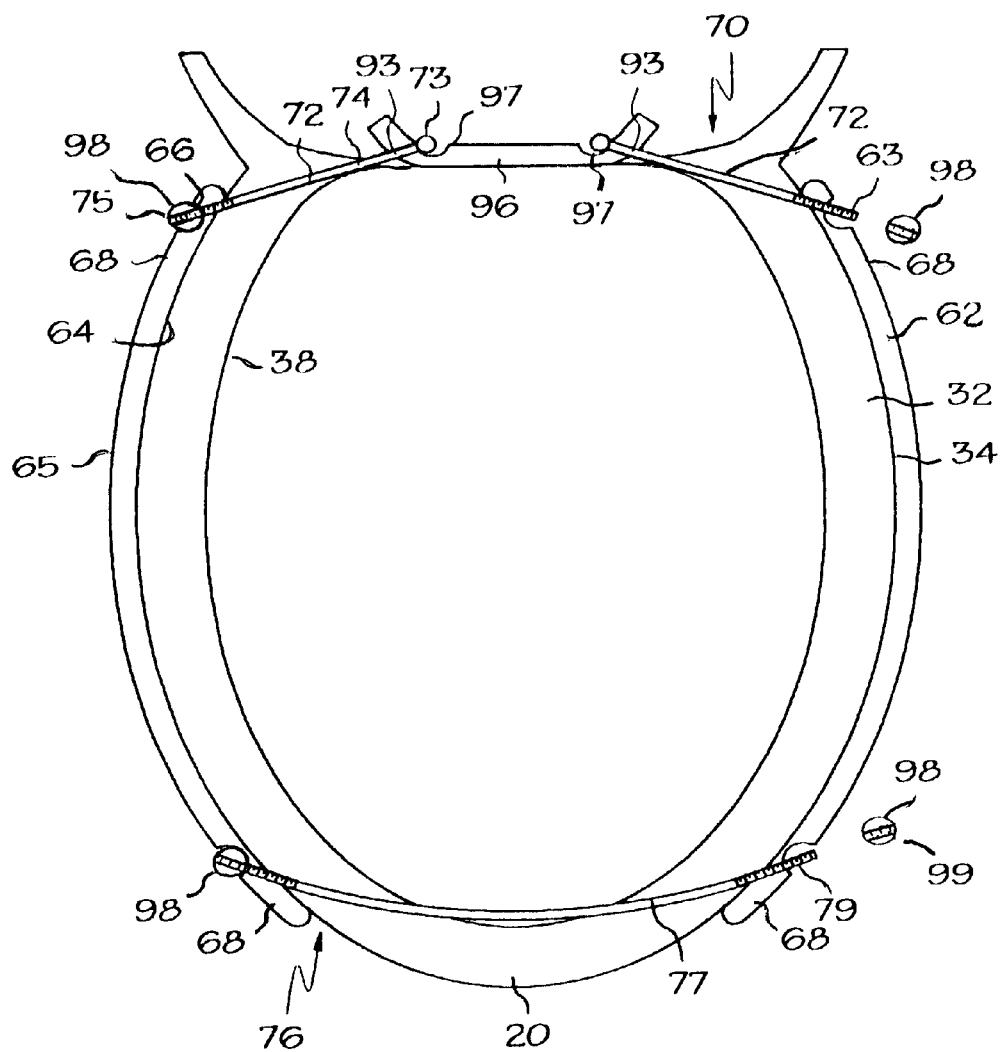
FIG. 8 is a vertical sectional view of an alternative embodiment of a device made in accordance with the present invention and positioned on the left ventricle.

Turning now to FIG. 8, connector 70 can also include a basal connector 96, which can be connected to the members 62 utilizing chords 72, one or more pins 72, and/or an apical connector 76.

Basal connector 96 preferably is configured to traverse or lie adjacent or on the atrial surface of the anterior annulus of an atrioventricular valve 50, such as the mitral valve 52, so as to assist in connecting or joining together end portions 68 of members 62 to assist in maintaining the position of the device 60 relative to itself and heart 10. It is further contemplated that a prosthetic valve and/or an annuloplasty ring may be used to assist in attaching and/or securing the basal connector 96 to the heart 10. Basal connector 96 may take the form of a portion of the prosthetic valve or annulus ring attached to the anterior annulus. Basal connector 96 is generally made of a suitable rigid biocompatible material, similar to member 62 as discussed above, and preferably includes a porous covering or outer surface to enhance tissue integrations, such as polyester fabric.

Basal pin 72, as exemplified in FIG. 8, preferably is an elongated screw, bolt, connector, or the like with a body portion 74, which can be sized to be insertable through aperture 63. Head portion 73 of the pin 72 preferably has a diameter greater than aperture 93 in the basal connector 96 so that pin 72 cannot be pulled therethrough. Moreover, head portion 73 can preferably be a rounded shape so that it can be seated and can assist in rotating and/or pivoting in counterbore opening 97. The body 74 can have an external threaded portion 75, which preferably extends along a portion of the body 74 opposite the head 73, or alternatively, along its entire length.

The threaded portion 75 is preferably adapted to receive a fastener 98, preferably having an internally threaded aperture 99, as will be discussed later, to assist in coupling the pin 72 to member 62. Pin 72 should have a length sufficient so that it can assist in connecting or joining a member 62 to basal connector 96, and preferably, the threaded portion 75 should extend outwardly beyond the counterbore opening 66 in member 62 so that a fastener (e.g., 98) can be attached.

An end cap, such the rounded fastener 98 illustrated in FIG. 8, can have an internally threaded aperture 99 either into or through its body, which can be sized and configured to threadably receive external threaded portion 75.

Connector 70 also can include an elongated apical pin 76 that is preferably curved or bowed as exemplified in FIG. 8. The body 77 of pin 76 preferably has externally threaded portions 79 adjacent its end portions, which are each likewise adapted to receive a fastener 98, preferably having an internally threaded opening 99, so as to assist in coupling pin 76 to members 62. It is contemplated that the entire body 77 could have external threads 79 which can receive a fastener 98 as discussed above. Apical pin 76 should have a sufficient length so that the threaded portions 79 extend outwardly beyond the respective counterbore openings 66 in members 62 so that a fastener 98 can be attached at each end.

Pins 72 and 76 and fastener 98 are each preferably made of a biocompatible material such as 3/6 stainless steel or CP titanium. Moreover, use of the same metal materials for the pins 72 and 76 and fastener 98, and member 62 can minimize the electrolytic corrosive action that can occur when dissimilar metal materials are used adjacent or in contact with each other. Moreover, the exterior surfaces of pins 72 and 76 and fastener 98 are preferably a porous material or have a porous finish or coating so as to enhance tissue integration.

Figure 9:
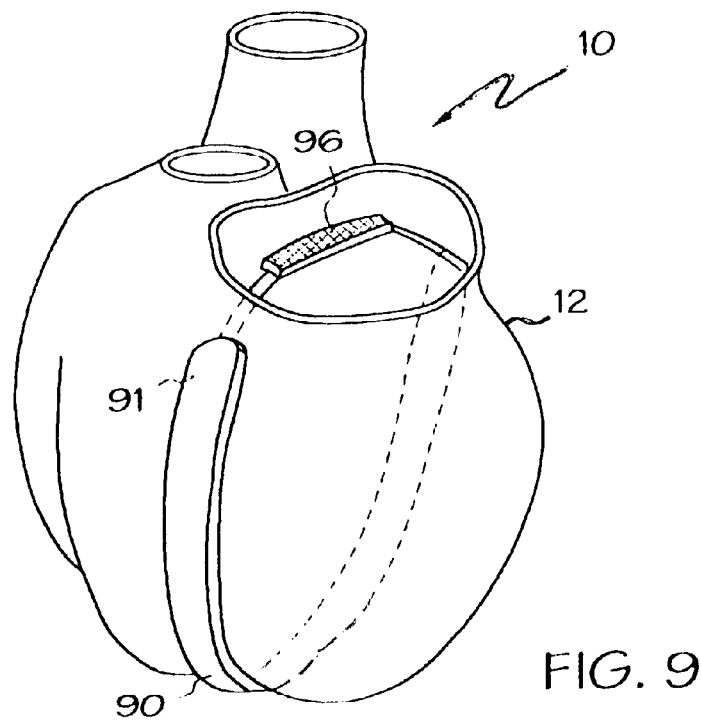
FIG. 9 is a perspective view of yet another alternative embodiment made in accordance with the present invention and positioned on the left ventricle.
Figure 10:
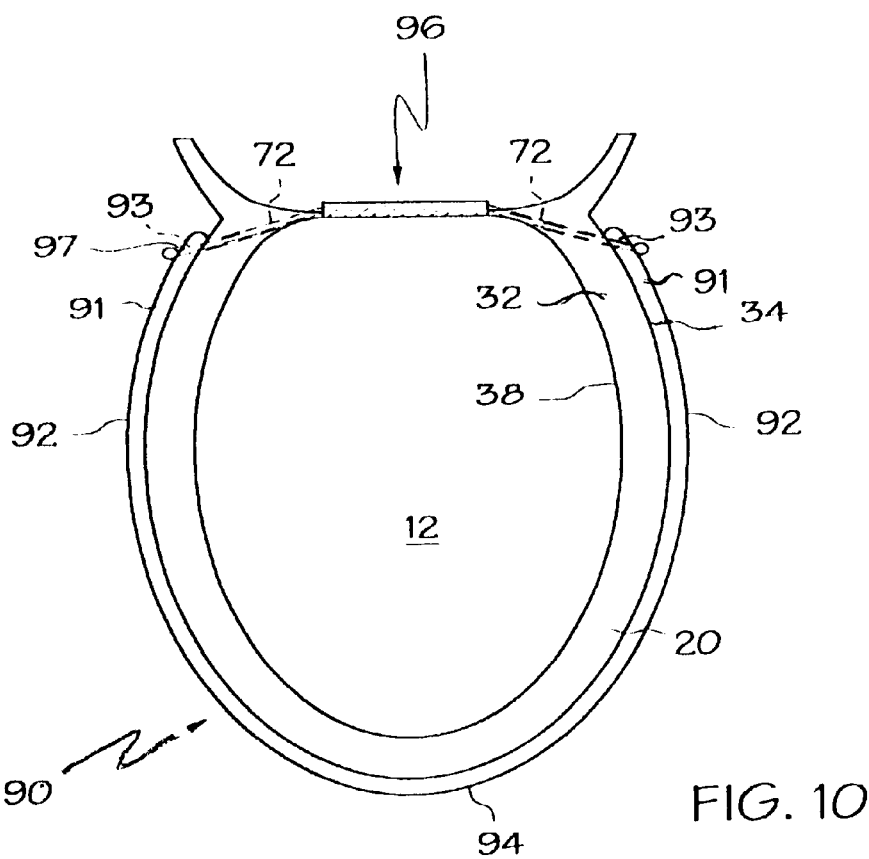
FIG. 10 is a vertical sectional view of the embodiment of FIG. 9.
Figure 11A:
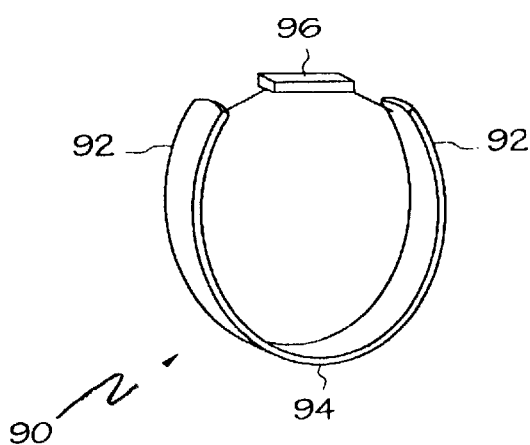
FIG. 11A is a perspective view of the embodiment of FIGS. 9–10 when the device is undeformed.
Figure 11B:
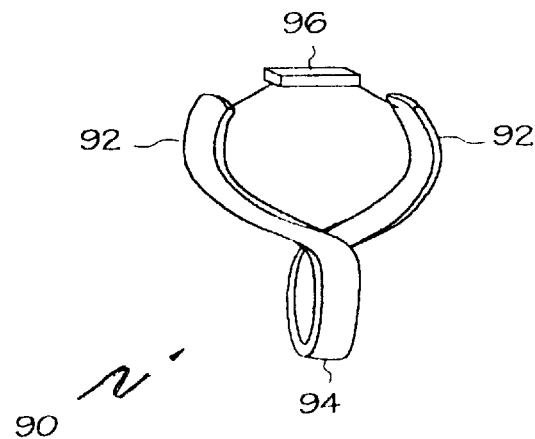
FIG. 11B is a perspective view of the embodiment illustrated in FIG. 11A when the device has been twisted due to ventricular contraction.

In an alternative embodiment of the present invention exemplified in FIGS. 9–10, a generally horseshoe or U-shaped harness or brace 90 can be used as device 60 to assist in reconfiguring or restructuring the heart 10, as detailed above. Brace 90 has at least two generally rigid portions 92, which are each generally similar to member 62 detailed above. The brace 90 can also include as a connector portion 94, which is generally flexible only in a plane tangent to the epicardial surface 34, and is generally configured to be positioned adjacent the epicardial surface 34 and extends around or spans the apical portion 20 of the heart 10. Connector portion 94 should be sufficiently flexible so that, as exemplified in FIGS. 11A and 11B, impedance to ventricular torsion during contraction is minimized and the heart 10 can twist as the heart 10 beats or contracts. While illustrated as generally a panel, connector portion 94 can take the form of any shape so long as it has an elastic quality, yet permits flexion only in the plane tangential to the epicardial surface 34.

The brace 90 also can preferably include a basal connector 96, which assists in connecting or joining the brace 90 to the heart 10. In the illustrated embodiment, basal connector 96 is joined to the brace 90 at or adjacent its end portions 91 using the apparatus and techniques discussed above.

Figure 12:
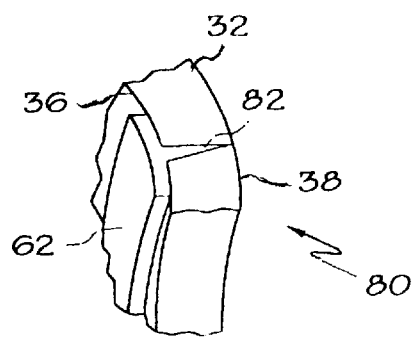
FIG. 12 is a vertical cross sectional view of one embodiment of an auxiliary fastener made in accordance with the present invention.
Figure 13:
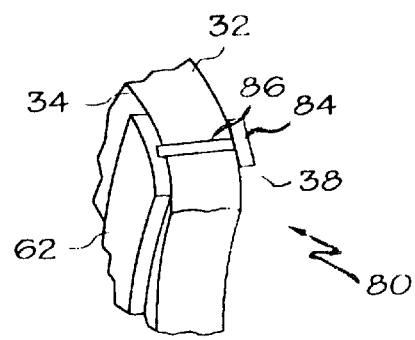
FIG. 13 is a vertical cross sectional view of another embodiment of an auxiliary fastener made in accordance with the present invention.

One or more auxiliary connectors 80, as exemplified in FIGS. 12 and 13, can also be used with the present invention to assist in maintaining the position of the device 60 relative to itself and to the heart 10, and more specifically, so that sideways displacement of the heart 10 relative to the brace 90 is minimized. Auxiliary connector 80 can take the form of a spike shaped object or pin 82 that is configured to penetrate the epicardial surface 34 into the cardiac tissue 32. Also, auxiliary connector 80 can take the form of a button 84 and cord 86. One end of the cord 86 can be attached or otherwise secured to the member 62 or brace 90, and it can extend inwardly into and through the cardiac tissue 32. A button 84 can be attached to or adjacent the other end of the cord 86 adjacent the endocardial surface 38. Button 84 can be made of any biocompatible material, and is preferably made of a material that enhances tissue growth around the button 84 to minimize the possibility of the formation of blood clots. It is further contemplated that other surgical attachment articles and techniques can be used in accordance with the present invention, such as screws, surgical staples and the like, to assist in fastening and securing the device in position, as desired.

In accordance with the teachings of the present invention, the device 60 should be so configured and positioned adjacent the heart 10 whereby the wall tension is reduced in accordance with LaPlace's theory of a chamber, which is as follows:

Chamber pressure=$K$*(tension of wall)/(radius of chamber),
wherein K is a proportionality constant.

As an illustrative example of one embodiment in accordance with the teachings of the present invention, calculations will be performed based on the following model as exemplified in FIGS. 3 and 5. It is assumed that the long axis of the left ventricle 12 of the heart 10 is 100 mm, that the equatorial or short axis of the chamber 12 is 70 mm, that the equatorial wall thickness "w" of the chamber is about 10 mm and the basal diameter of the heart 10 is 60 mm. An arbitrary slice or plane of the left ventricle 12 will be analyzed to illustrate local dimensional computations for the present invention.

Furthermore, this model will assume that the inner radius "$R_1$" (of the slice or plane) of the unrestricted heart 10 (see, e.g., FIG. 3) is about 28.982 mm and that the heart 10 has an outer radius of about 38.406 mm. As is known to those skilled in the industry, the width "w" and radius "$R_1$" can be directly obtained from high-resolution imaging, such as an echocardiogram, or preferably, by computation based on an assumed geometric model. The ratio of the restraint contract pressure of the left ventricle 12 of the device 60 to the cavity pressure can vary from 1 to about 2. This example will further assume that the allowed ratio of the restraint contact pressure of the left ventricle 12 of device 60 to the cavity pressure is to be limited to a maximum of about 1.5, which is represented by symbol K in the mathematical formulas below. Also, it is desired to achieve an altered radius "$R_2$" of the left ventricle 12 to 80% of its original radius $R_1$, and as such:

$$R_2 = 0.8 * R_1$$

$$R_2 = 0.8 * 28.982 \text{ mm}$$

$$R_2 = 23.186 \text{ mm}$$

In order to calculate the radius of curvature "g" of the inner surface 64 of member 62 in the transverse plane, the following formula can be used:

$$g = (w + R_2) \div (k - 1)$$

$$g = (9.424 \text{ mm} + 23.186 \text{ mm}) \div (1.5 - 1)$$

$$g = (32.61 \text{ mm}) \div 0.5$$

$$g = 65.22 \text{ mm}.$$

Now that the value of radius of curvature of the inner surface 64 "g" has been calculated, the angle "θ" between the line $g_1$ (joining the center of curvature of the member 62 with one margin, in this plane, of the contact area between inner surface 64 and the epicardial surface 34) and line $g_2$ (joining the same center of curvature with the center of the inner surface 64 in the same plane) can be calculated using the following formula:

$$\theta = (\pi/2) * [R_2 - R_1] \div (R_2 + w + g)$$

$$\theta = (\pi/2) * [28.982 \text{ mm} - 23.186 \text{ mm}] \div (28.982 \text{ mm} + 9.424 \text{ mm} + 65.22 \text{ mm})$$

$$\theta = (\pi/2) * [5.796 \text{ mm}] \div (103.636 \text{ mm})$$

$$\theta = 0.09063 \text{ radius or } 5.332 \text{ degrees}$$

Using the formula below, the distance inwardly that the heart 10 should be displaced can be calculated so that the desired restructuring can be achieved. If "e" is the distance that the center of either member 62 is to be separated from the absolute center of a remodeled ventricle in this plane, then:

$$e = [(g + w + R_2) * \cos \theta] - g$$

$$e = [(65.22 \text{ mm} + 9.424 \text{ mm} + 23.186 \text{ mm}) * \cos 5.332 \text{ degrees}] - 65.22 \text{ mm}$$

$$e = 32.21 \text{ mm}.$$

As such, twice e or (2*e) is 64.42 mm, and this is the preferred distance separating the oppositely disposed inner surfaces 64.

Based on the calculation, the wall of the heart 10 needs to be displaced or moved inwardly about 6.20 mm from the unrestrained position to achieve the desired restructure or reconfiguration whereby wall tension is adjusted, as desired. Also, using the formula 2θg to calculate the desired contacting width of the inner surface 64, which is about 11.68 mm in this example.

To position the device 60 into a body (e.g., the thoracic cavity) and around an existing natural heart 10, a high resolution image, such as a standard echocardiogram, or other analysis of the heart 10 is preferred so that certain anatomical measurements can be recorded and calculated, as detailed above. While the present application only includes one set of mathematic calculations to optimize the present invention, it is contemplated that measurements will need to be taken along several axes, planes, locations or positions along the longer axis of the chamber. Pre-surgical calculations are preferred so that the device 60 can be optimally configured and sized, as desired, before surgery to minimize surgical time.

Open heart thoracic surgery may be required to implant device 60. Alternatively, intracardiac components may be placed and positioned by wall penetrating needles and or insertion of components through the left atrial appendage of a beating heart 10. Clinically sufficient anesthesia is administered and standard cardiac monitoring is employed to the patient and then, the thoracic cavity, where the heart 10 is usually situated, is opened using standard thoracic surgical procedures, which are known to those skilled in the art.

Once the thoracic cavity is opened, if an open heart procedure employed in the present invention, circulation of blood to the natural heart 10 should be bypassed so the present invention can be inserted on and/or into the patient. Referring back now to FIG. 2, the superior vena cava 22, the inferior vena cava 24, and aorta 26 are cannulated. The circulatory system is connected to as a cardiopulmonary bypass machine so that circulation and oxidation of the blood are maintained during the surgical procedure. By way of example, the procedure discussed in detail will be for insertion of the present invention 60 to restructure or reconfigure the left ventricle 12.

Turning now to FIGS. 4–6, members 62, which may be customized according to the anatomical measurements and calculations, are preferably positioned adjacent or against the epicardial surface 34 in predetermined locations relative to each other and relative to the chamber (e.g., left ventricle 12). As exemplified in FIG. 4, the members 62 can be positioned about 180 degrees relative to each other, and in FIG. 6, about 120 degrees relative to each other, as desired. The members 62 can be temporarily attached to the heart 10 using temporary sutures or a suitable adhesive so that the connectors 70 can be attached and secured without moving members 62.

Connector 70 is attached or secured to member 62 so that portions of the heart 10 are urged inwardly, as desired. In one embodiment, chord 72 can be inserted through an aperture 63 in one of the members 62, and inserted through the cardiac tissue 32, preferably using a surgical needle, whereby the chord 72 can be extended across the cavity 13, into the cardiac tissue 32 on the other side of the chamber (e.g., left ventricle 12), and then finally, through a corresponding aperture 63 in the oppositely disposed member 62. This can be repeated with as many connectors 70 as necessary so that the members 62 are positioned and secured, as desired. Chord 72 can be either cut or sized, or can be provided pre-sized and then secured to the member 62, such as by tying a suture knot, so that chord 72 is taut between or among the members 62, and so that members 62 are positioned as a predetermined distance apart, (2*e), as detailed above, so that the heart 10 is restructured or reconfigured, as desired.

Alternatively, it is contemplated that chords 72 may be inserted through apertures 63, preferably adjacent the end portions 62, and positioned so as to enhance tissue formation around chords 72. In one embodiment, chord 72 may be inserted through apertures 63 and positioned so that it extends adjacent the endocardial surface 38, or through the cardiac tissue 32 itself, to connect or join the members 62.

In an alternative embodiment utilizing a basal connector 96, the basal connector 96 can be secured to the annulus of the mitral valve 52, using sutures and/or a suitable adhesive. The basal pin 72 can have a needle or other sharp instrument attached to the end opposite the head 73. A suture can be interposed between the needle and pin 72 to assist in inserting the pin 72 through the cardiac tissue 32. The needle can be inserted through aperture 93 in basal connector 96, through cardiac tissue (e.g., the ventricular free wall and/or the atrioventricular wall 42), and then through aperture 63. The protruding threaded portion 75 can have a fastener 98 attached, preferably screw on and attached to the pin 72. To enhance attachment and to minimize the opportunity for fastener 98 to become unsecured, an adhesive or additional fastening device may be used to assist in securing the members 62 in place, as desired. The portion of pin 72 extending beyond the fastener 98 can be removed. Fastener 98 is preferably attached to pin 72 so that it is seated in the counterbore opening 66 and head 73 is preferably seated in counterbore opening 97 so as to assist in providing a ball and socket like and/or pivot joint, which can allow some rotational movement of the device 60 during contraction of the heart 10.

Apical pin 76 can also be used as part of connector 70, and can preferably have a needle or other sharp instrument attached adjacent one end of the body 77. The needle is then preferably inserted through the counterbore opening 66, aperture 63, preferably through or adjacent cardiac tissue 32 of the apical portion 20 of the heart 10, through the aperture 63 and counterbore opening 66 of the oppositely disposed member 62. Threaded portions 79 should preferably protrude from each of the counterbore openings 66 in members 62. As discussed above, fastener 98 preferably having an internal threaded portion 99 can be is threaded on and secured to each of the threaded portions 79 so as to assist in positioning members 62, as desired. The portion of pin 76 extended beyond fastener 98 can be sized or removed. Fasteners 98 are each preferably likewise seated in their respective counterbore openings 66 so as to assist in providing a ball and socket joint or a pivot joint, as mentioned above.

When device 60 is provided as brace 90, brace 90 and its rigid portions 92 are positioned adjacent or against the epicardial surface 34, as were the members 62 while connector portion 94 is positioned or wrapped around the apical portion 20 of the heart 10 to assist in connecting or joining the rigid portions 92 together, and to assist in maintaining the brace 90 properly positioned adjacent the heart 10 to provide the desired restructuring.

A basal connecter 96, as described above, can be affixed to the annulus of the mitral valve 52. Connectors 70, such as chords 72, or alternatively basal pins 76, can be used to connect or join the other ends of the rigid portions 92, as detailed above.

If auxiliary fasteners or connectors 80 are provided on or along members 62 and/or brace 90, they are inserted and secured to the heart 10.

Once the device 60 is properly positioned and secured, termination of a cardiopulmonary bypass, if used, is attempted and, if successful, the thoracotomy is closed.

An alternative method for positioning the present invention includes removing the natural heart 10 from the patient, positioning all the components of the present invention 60, as discussed above, and auto-transplanting the natural heart 10 back into the patient using standard cardiectomy and cardiac transplant techniques known in the industry.

Having shown and described the preferred embodiments to the present invention, further adaptations of the activation device for the living heart as described herein can be accomplished by appropriate modifications by one of ordinary skill in the art without departing from the scope of the present invention. For example, the present invention can be used with any one or even as a plurality of the various chambers of a living heart, and also could be used with different structural embodiments to restructure he chamber. Several such potential modifications have been discussed and others will be apparent to those skilled in the art. Accordingly, the scope of the present invention should be considered in terms of the following claims and is understood not to be limited in the details, structure and operation shown and described in its specification and drawings.

I claim:

1. A static device for use with a heart having at least one chamber, said device comprising:

a plurality of members configured to be positioned adjacent the epicardial surface of the heart; and a connector joining the members;

wherein said device is positioned in a spaced relationship relative to each other to reconfigure the chamber of the heart as at least two contiguous communicating portions of truncated ellipsoids.

2. A static device for use with a heart having at least one chamber, said device comprising:

a plurality of members configured to be positioned adjacent the epicardial surface of the heart; and at least one connector for extending through the chamber joining the members together.

3. A static device for use with an unrestricted heart having an outer wall and at least one chamber, said device comprising:

a plurality of members configured to be positioned adjacent the epicardial surface of the heart; and a connector joining the members;

wherein said members are fixed in a spaced relationship relative to each other such that at least two discrete portions of the outer wall are displaced inwardly from the unrestricted position.

4. The device of claim 3, wherein said members comprise a rectangular shape.

5. The device of claim 3, wherein said members comprise an inner surface having a convex curved configuration toward the epicardial surface.

6. The device of claim 3, having first and second members, wherein said first and second members are positioned in a spaced relationship relative to each other about 180 degrees apart.

7. The device of claim 3, having a first member configured to be positioned adjacent the anterolateral surface of the chamber, and a second member configured to be positioned adjacent the posteromedial surface of the chamber.

8. The device of claim 3, having first, second and third members, said first, second, and third members are positioned in a spaced relationship relative to each other about 120 degrees apart.

9. The device of claim 8, wherein the first member is configured to be positioned adjacent the anteroseptal portion of the chamber, the second member is configured to be positioned adjacent the posteroseptal portion of the chamber, and the third member is configured to be positioned adjacent the posterolateral portion of the chamber.

10. The device of claim 3, wherein said device comprises a pad adjacent an inner surface of at least one member.

11. The device of claim 10, wherein the pad comprises low durometer polymer.

12. The device of claim 10, wherein the pad comprises a cushion.

13. The device of claim 12, wherein said cushion comprises a gel-filled cushion.

14. The device of claim 12, wherein said cushion comprises a fluid-filled cushion.

15. The device of claim 3, wherein said connector comprises a chord.

16. The device of claim 15, wherein said connector comprises heavy braided polymer impregnated polyester suture core with a polyester sleeve.

17. The device of claim 15, wherein said connector comprises a heavy monofilament polypropylene suture.

18. The device of claim 15, wherein said connector comprises expanded polytetrafluoroethylene.

19. The device of claim 3, wherein said connector comprises a pin.

20. The device of claim 19, wherein said members each comprise an aperture and wherein said pin comprises a threaded portion adjacent one end of said pin, and a fastener receivable by said pin.

21. The device of claim 3, comprising at least one fixation device on said members configured for insertion into the heart.

22. The device of claim 21, wherein the fixation device comprises a pin for penetrating the wall of the heart.

23. The device of claim 21, wherein the fixation device comprises a button for positioning adjacent the interior surface of the heart and a cord joining said connector and said button.

24. The device of claim 3, wherein said connector comprises a band configured for extending around the chamber and joining the first member and the second member.

25. The device of claim 3, comprising a generally U-shaped harness having a first rigid portion configured to be positioned adjacent the anterior portion of the chamber, a second rigid portion configured to be positioned adjacent the posterior portion of the chamber, and a flexible portion interposed between said first and second portion and configured to be positioned around the apical portion of the heart.

26. The device of claim 25, comprising a basal connector configured to be interposed between the first and second rigid portions of said harness.

27. The device of claim 25, wherein said basal connector is configured to be attachable to the annulus of an atrioventricular valve.

28. A method for reducing the wall tension on one of the chambers of the heart, comprising the steps of:
affixing a static brace external to the one chamber of the heart to reconfigure the chamber into at least two contiguous portions of truncated ellipsoids.

29. The method of claim 28 wherein the brace has at least two members, a fastener on the members, and a connector, the method further comprising the step of inserting the fastener into the heart wall of the heart.

30. The method of claim 29 further comprising the step of positioning a portion of the connector adjacent the epithelium of the heart.

31. The method of claim 30 further comprising the step of attaching the connector to an atrioventricular valve.

32. The device of claim 3, wherein said connector is configured to lie adjacent the atrial surface of the anterior annulus of an atrioventricular valve.

33. The device of claim 32, wherein said connector is configured to lie adjacent the mitral valve.

34. The device of claim 3, wherein said connector comprises:
a first connector configured to be positioned adjacent the endocardium of the chamber; and
a second connector configured to be positioned adjacent the atrial surface of the anterior annulus of an atrioventricular valve.

35. The device of claim 34, wherein said second connector is curved.

36. A device for reconfiguring a chamber of a natural heart, said device comprising:
a structure having a first and a second portion, that encircles the natural heart and is adapted to exert a constant inward displacement on at least two discrete portions of the exterior surface of one and only one chamber of the natural heart.

37. The device of claim 36, wherein said structure comprises a plurality of interconnected members.

38. The device according to claim 36, wherein said device has a structural shape adapted to exert differential displacement at predetermined locations of the exterior surface of the natural heart.

39. The device according to claim 36, wherein said first portion of said structure lies adjacent a basal surface of the natural heart.

40. The device according to claim 36, wherein said second portion of said structure lies adjacent an apical surface of the natural heart.

41. The device according to claim 36, wherein a first portion of said segment lies adjacent an anterolateral surface of a left ventricle.

42. The device according to claim 36, wherein a second portion of said segment lies adjacent a posteromedial surface of a left ventricle.

43. The device according to claim 36, wherein said device encircles at least one chamber of the natural heart.

44. The device according to claim 43, wherein said first portion of said structure lies adjacent a basal surface of said chamber of the natural heart.

45. The device according to claim 43, wherein said chamber is a ventricle.

46. The device according to claim 43, wherein said chamber is an atrium.

47. The device according to claim 43, wherein said second portion of said structure lies adjacent an apical surface of said chamber of the natural heart.

48. The device according to claim 47, wherein said chamber is a ventricle.

49. The device according to claim 36, wherein said device has at least one deformable portion and is adapted to torsionally deform as the natural heart beats.

50. The device according to claim 36, wherein said device has an inner surface and said inner surface is convex toward the surface of the natural heart.

* * * * *

Adverse Decisions in Interference

Patent No. 6,409,760, Dr. David B. Melvin, DEVICE AND METHOD FOR RESTRUCTURING HEART CHAMBER GEOMETRY, Interference No. 105,452, final judgment adverse to the patentees rendered August 16, 2006, as to claims 1-50.

*(Official Gazette April 17, 2007)*